(12) United States Patent
Granja Filho

(10) Patent No.: US 8,828,030 B2
(45) Date of Patent: Sep. 9, 2014

(54) INSERTABLE PROSTHESIS AND PROSTHESIS BOARD FOR ANASTOMOSIS

(76) Inventor: Luiz Gonzaga Granja Filho, Recife/PE (BR)

(*) Notice: Subject to any disclaimer, the term of this patent is extended or adjusted under 35 U.S.C. 154(b) by 781 days.

(21) Appl. No.: 12/303,536

(22) PCT Filed: Jun. 6, 2007

(86) PCT No.: PCT/BR2007/000145
§ 371 (c)(1),
(2), (4) Date: Mar. 30, 2009

(87) PCT Pub. No.: WO2007/140561
PCT Pub. Date: Dec. 13, 2007

(65) Prior Publication Data
US 2010/0010516 A1   Jan. 14, 2010

(30) Foreign Application Priority Data

Jun. 6, 2006 (BR) .................................. 0602385

(51) Int. Cl.
*A61B 17/08* (2006.01)
*A61F 2/06* (2013.01)
*A61B 17/11* (2006.01)

(52) U.S. Cl.
CPC ......... *A61F 17/11* (2013.01); *A61B 2017/1139* (2013.01); *A61B 2017/1107* (2013.01); *A61F 2/064* (2013.01); *A61B 2017/1135* (2013.01)
USPC ...................................................... 606/153

(58) Field of Classification Search
CPC ........... A61B 17/11; A61B 2017/1135; A61B 2017/1107; A61B 2017/1139; A61B 2017/1132; A61F 2/064
USPC ............... 606/153, 154, 155, 156, 213, 304; 128/887
See application file for complete search history.

(56) References Cited

U.S. PATENT DOCUMENTS

| 3,254,650 | A | 6/1966 | Collito |
| 3,265,069 | A | 8/1966 | Healey, Jr. et al. |
| 3,774,615 | A | 11/1973 | Lim et al. |
| 4,366,819 | A | 1/1983 | Kaster |
| 6,503,258 | B1 * | 1/2003 | Filho ............................. 606/153 |
| 2004/0024415 | A1 * | 2/2004 | Perouse ........................ 606/153 |

OTHER PUBLICATIONS

Merriam-Webster definition of "caliber" as attained Apr. 3, 2012; http://www.merriam-webster.com/dictionary/caliber.*

* cited by examiner

*Primary Examiner* — Jonathan W Miles
(74) *Attorney, Agent, or Firm* — Volpe and Koenig, P.C.

(57) ABSTRACT

Prosthetic devices are provided used for anastomosis of extremity with lateral, extremity with extremity and lateral with lateral without clamping and sutureless or with quick clamping sutureless, in which the graft is inserted in at least one of the intraluminal parts of the tubular member of the insertable prosthesis, the flanges including lateral inserts allowing the configuration of different prosthesis sets. The present invention also describes a board of prostheses including one flange with multiple holes through which intraluminal parts or occluders will be inserted, according to the need of the anastomosis to be carried out. The invention also includes prostheses in which the grafts cover only externally their extraluminal parts.

5 Claims, 18 Drawing Sheets

Prosthesis 1

Slot detail

Slot detail

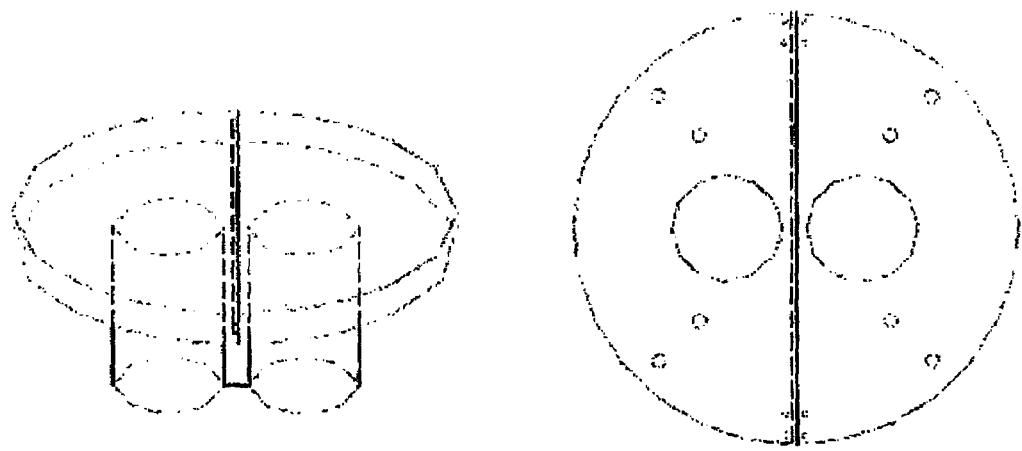

Slot detail
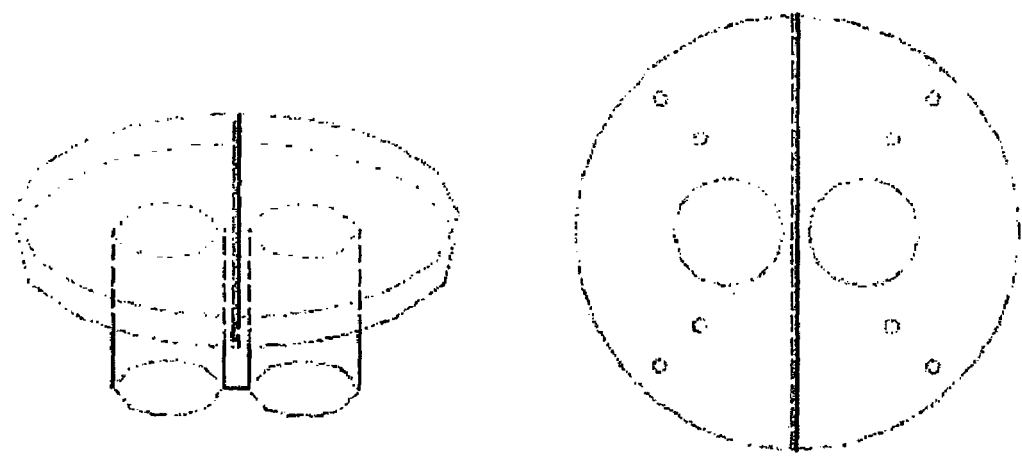

Slot detail

ORIFICIOS PARA PASSAGEM DOS PONTOS PARA REFORCO DA UNIÁO ENTRE AS PRÓTESES.

DETALHE DO ENCAIXE

Slot detail

Slot detail

Slot detail

Slot detail

Slot detail

Occluder

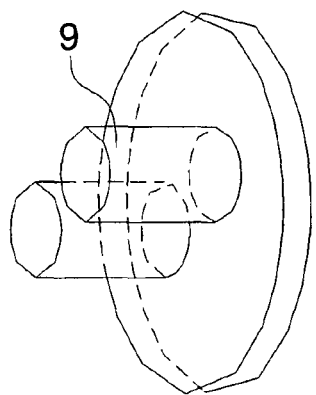
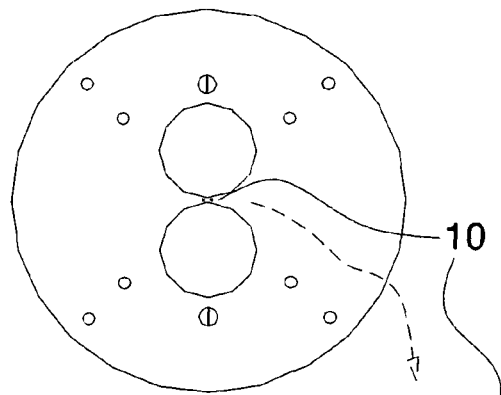
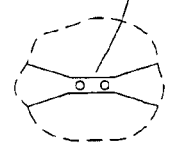
FIG. 11A  FIG. 11B
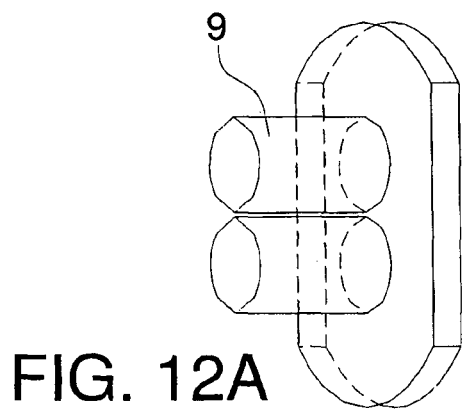
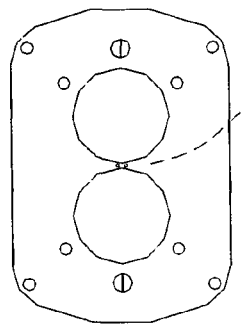
FIG. 12A  FIG. 12B
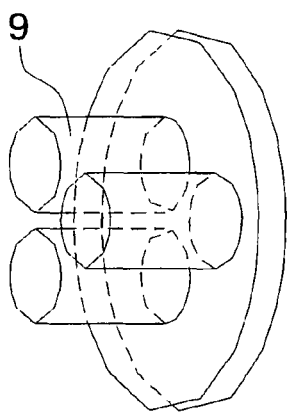
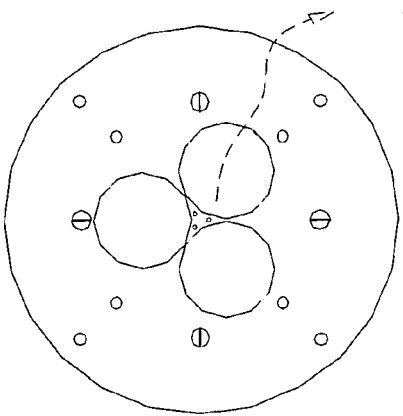
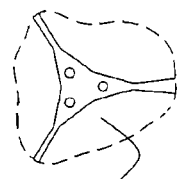
FIG. 13A  FIG. 13B

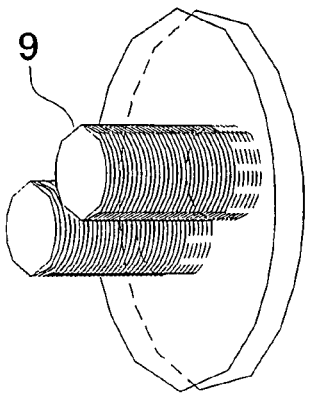 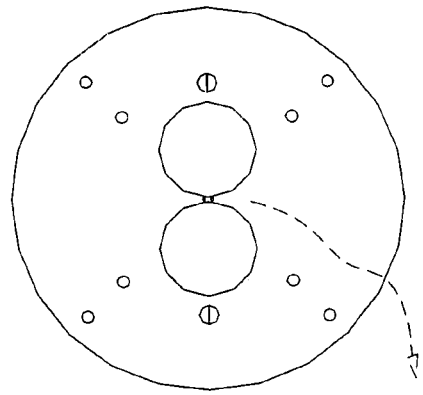
FIG. 14A    FIG. 14B
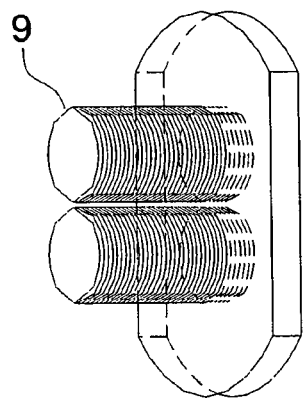 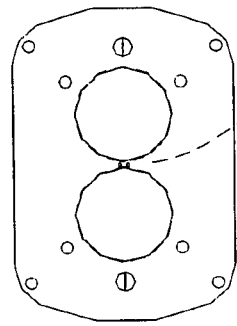
FIG. 15A    FIG. 15B
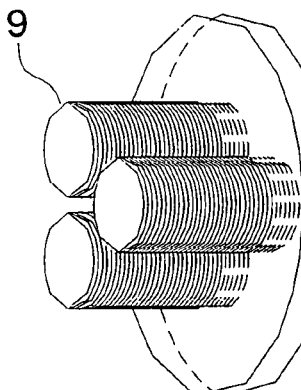 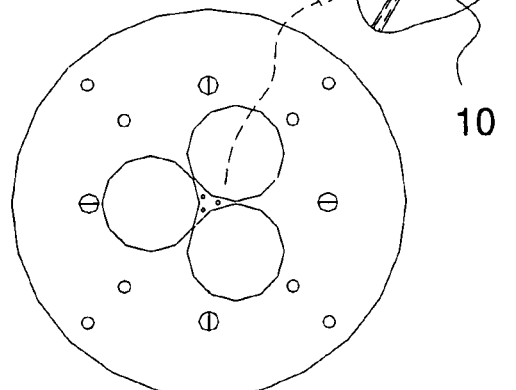
FIG. 16A    FIG. 16B

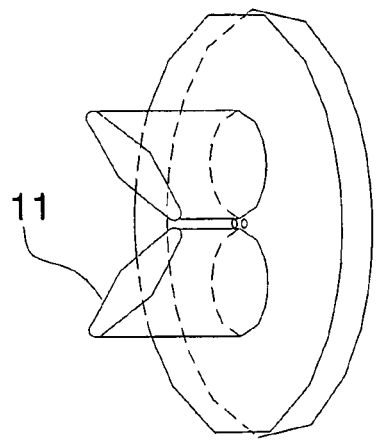 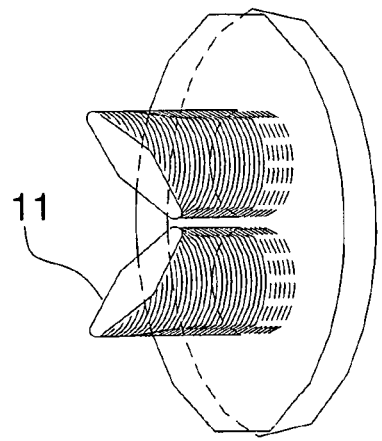
FIG. 17A    FIG. 17B
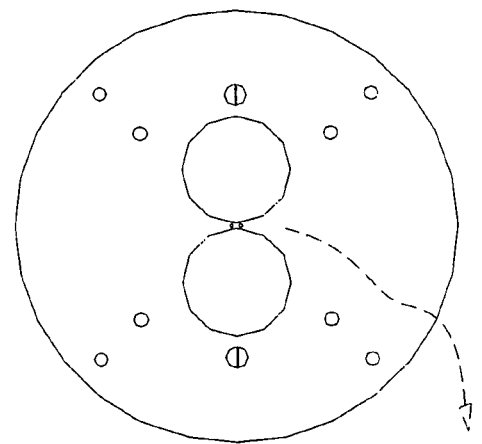

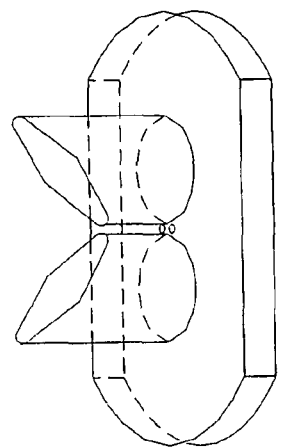 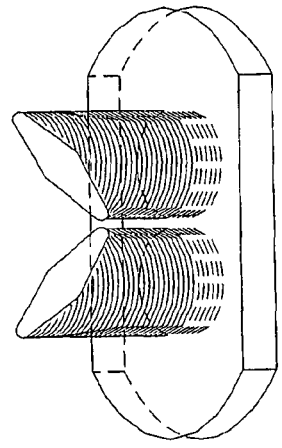
FIG. 18A                FIG. 18B
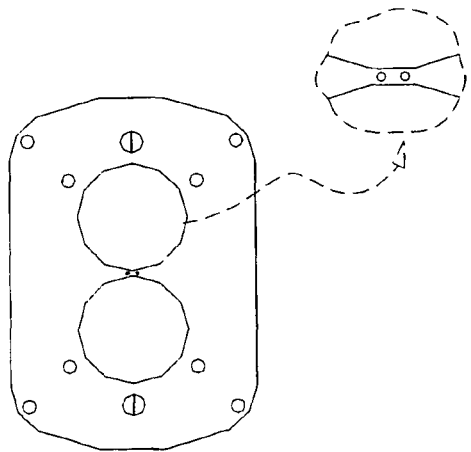
FIG. 18C

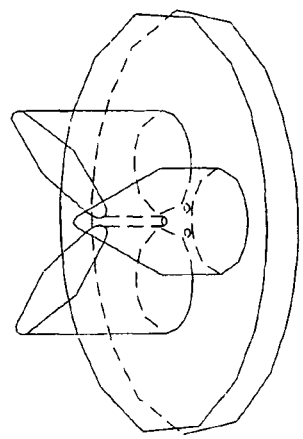 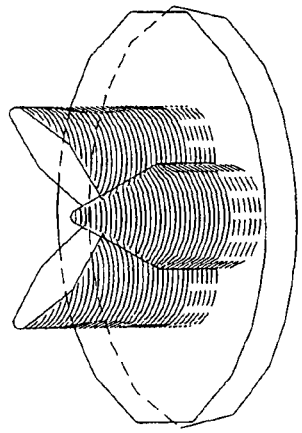
FIG. 19A　　　　　　　FIG. 19B
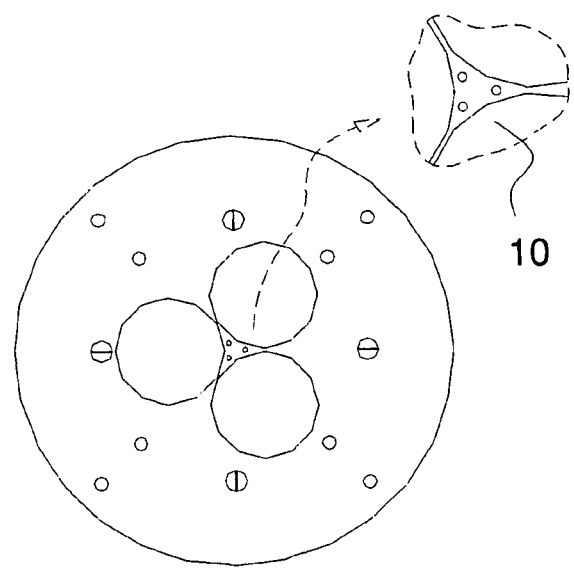
FIG. 19C

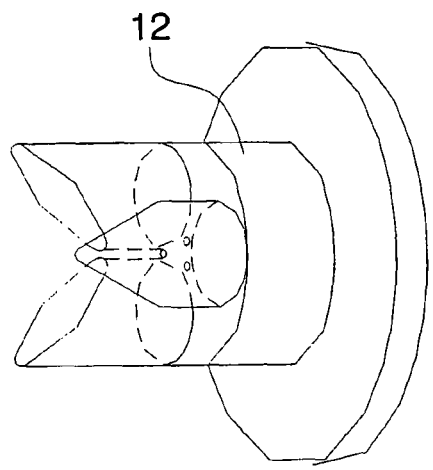
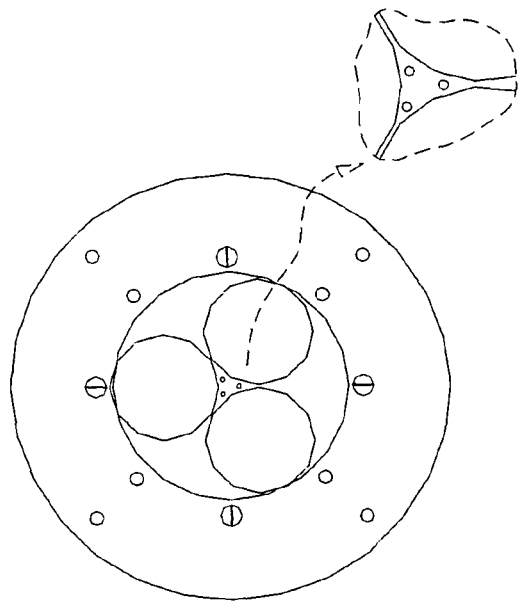
FIG. 20A         FIG. 20B
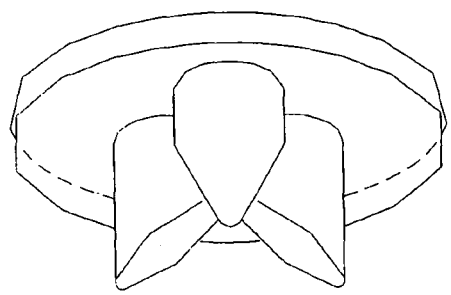
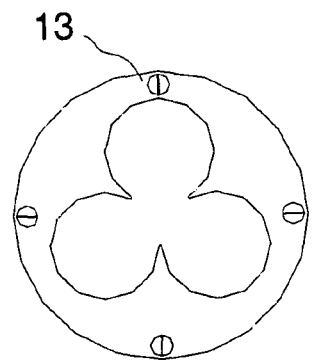
FIG. 21A         FIG. 21B

INSERTABLE PROSTHESIS AND PROSTHESIS BOARD FOR ANASTOMOSIS

FIELD OF THE INVENTION

The present invention refers in general to anastomotic devices and, more specifically, to a prosthetic device of multiple lateral inserts allowing anastomosis without clamping and sutureless or, in cases of organs with normal walls, with quick clamping sutureless, where a vascular graft or any other is inserted into the lumen of each prosthesis and turned by casing in order to cover part of it, which will remain inside the graft (vein, artery or tissue), being fixed onto the tubular member of the prosthesis by a circular stitch or other methods. The flange of the prosthesis has several spaced out openings on its periphery, allowing the prosthesis to be sutured in the tissue, vein, artery or any other organ outside the anastomosis. Moreover, the flange of the prosthesis also has at least one lateral insert that allows the prostheses to be tightly united one to the other. The present invention also refers to a board of prostheses, with at least two intraluminal parts of different types, calibers and shapes that may be activated or deactivated according to the needs of the anastomosis.

DESCRIPTION OF THE PRIOR ART

A prior art presents several trials provide solutions for anastomotic devices projected to correct vascular abnormalities, which present the following typical features:

The North-American U.S. Pat. No. 3,254,650, of Jun. 7, 1966, describes a method and devices to execute anastomosis procedures by applying with adhesive two separated connectors in a body member and removing this body member portion contained among the connectors, joining the said connection devices for joining the remaining portions of the body member.

The U.S. Pat. No. 3,265,069, of Aug. 9, 1966, describes devices or instruments for use by surgeons in reunion of body ducts, which in the course of operations were separated. The instruments comprise a pair of elongated similar elements and articulatedly connected, in an intermediary manner, and with an support for finger retention in a distal end, comprising a generally cylindrical shape with a cylindrical channel that passes through it in the other distal end, in order to receive tubular body ducts kept by the instrument while the body ducts are reconnected.

U.S. Pat. No. 3,774,615, of Nov. 27, 1973, describes a device to connect the end of interrupted tubular organs without sewing, comprising a connecting ring on which the end of the interrupted organ are pulled, the ring is preferably locked up by a fixation resource. The ring and fixation resource are made of inert material, and preferably a hydrophile gel that can be dilated until its equilibrium or can be a hydrogel incompletely dilated, which is submitted to additional dilatation where it is applied. The connecting ring can be supplied with a groove and can be placed in a ring shaped fixation resource and kept there joining it to the fixation resource in the groove or simply kept by a screw. Two connection rings can also be used and kept joined by a coupling member.

The document U.S. Pat. No. 4,366,819, of Jan. 4, 1983, describes an anastomotic joint for surgery with a graft of coronary artery deviance comprising a mounting of four elements including a cylindrical tube with at least one locking indentation of ring flange in one influx end and a plurality of grooves of locking ring in a flow end; a ring flange with a central opening and a plurality of long and short spigots, the long spigots are engaged in the locking indentation, with a graft engaged among them; a fixation ring with a central opening and a plurality of spigots positioned around the opening; and a locking ring with a opening with a plurality of locking ring edges for engaging with the locking ring grooves. In surgical implants, an aortic wall with a hole engages between the ring flange and the fixation ring and is kept in this position by spigots of the fixation ring, and the four elements engage together forming an integral anastomotic joint. A first alternate modality includes an anastomotic joint of three elements with a combination of fixation ring and locking ring. A second alternate modality includes an anastomotic joint of four elements with a slightly jolted end in a influx end, exposing the graft material in the anastomotic "ostium".

Other prior arts are equally mentioned, base don some information of "The Cardiothoracic Surgery Network". The "Simmetry Aortic Connector System", developed by St. Jude Medical, is a connector made with nitinol, selected by vein diameter with an adventitia removed to allow adjust of the connector and to prevent its displacement by the blood current. Then, the device may make an angle of 90° with the aorta. Among the disadvantages, there is the fact that it can be used only in extreme cases due to the difficult usage of this technique; it did not obtain a satisfactory result in many surgeries and it is being drowned out of market by the manufacturer; it is not applicable in calcified aorta; presents suture; presents contact with blood flow (foreign body); it does not widen the anastomosis area (restrictive anastomosis); performs only one anastomosis at a time; it is a product restrict to end-to-side anastomosis; a great mobilization of the venous graft occurs, damaging it, and can eventually form thrombus; there is a risk of perforation of the posterior wall of aorta; and the adventitia is removed (most resistant vascular layer).

Other known device is the PAS-Port™ System, a device used in 3 steps, and the vein wall is mounted over the device and is manually reversed on it, by tool and adapted to aorta with a angle of 90°. The method alerts that the surgeon shall select with due care the point of aorta and the vein size. The device is made of stainless steel and is available in only one size that allows the use of veins with external diameter of 4 to 6 mm, aorta with an internal diameter of 18 mm. It is available in only one size, limiting its applicability. As disadvantages of this prior art, the device has contact with blood flow (foreign body); it does not widen the anastomosis area (restrictive anastomosis); it uses veins with external diameter of 4 to 6 mm and aorta with an internal diameter of 18 mm; it does not perform multiple nor visceral anastomosis; it performs just only end-to-side anastomosis; a great mobilization of the used biological graft occurs, damaging its inner layer, which generates the formation of thrombus; there is a big risk of kinking at the origin (angle of 90°) and risk of posterior wall perforation in the aorta at the moment the device is introduced under its light; the suture is substituted with disadvantages by stainless steel (9 pins, distant among them, maximizing the risk of bleeding).

Also as prior art, there is the CorLink Device, currently commercialized by Ethicon/Johnson & Johnson, that allows the creation of anastomosis between the ascending aorta and a saphenous vein segment. Aortic Anastomotic Device (AAD) is a self-expanded device with extra luminal nitinol constituted by a de um central cylinder with five interconnected elliptical arches and 2 groups of 5 pins in the end portion of the cylinder. The pins, after the eversion of venous walls in the device, fix the aggregate penetrating into the venous graft wall. A blade makes an opening in the wall of aorta and permits the coupling of AAD, which also fix the wall of aorta by pins. With this device: it poses a serious risk of bleeding, especially in friable aortas, thin, calcified or fibrous, restricting its applicability, also with risks, even in aortas with normal walls; in small gauge anastomosis, there is a risk of thrombosis, hyperplasia, intimal proliferation and fibrosis (reaction to foreign body type in origin of anastomosis) with consequent stenosis resulting in occlusion of anastomosis; sutures are used in some cases; there is cases of infarction caused by equipment; there is a recurring need of re-operations in patients; the device presents contact with blood flow (foreign body); it is not flexible; it does not multiple anastomosis; an inadequate mobilization of venous graft occurs, and can cause damage to its intimal layer, it could form thrombus; it is used only in extreme cases because it is a technique of complex usage; the suture is substituted by stainless steel in contact with blood flow.

Another known device is the St Jude Distal Connector that consists of a stainless steel clip mounted on a catheter, comprising a balloon for subsequent expansion and connector mounting. The catheter is introduced backward from the end, by doing a small hole in the anastomosis site, the clip fixes the vein in the hole, the catheter goes to coronary and releases the connector. The catheter is removed and a suture is done in side-to-side anastomosis. With St Jude Distal Connector, occurrence of leakage problems were detected in 20% of the used connectors; the use of a metallic clip requires due care for handling to avoid distortion in the anastomosis; late angiographies reveal smaller circular diameter of anastomosis made with o St. Jude Distal Connector, when compared to controls made with conventional suture; there is remarkably risk of bleeding and the graft is very mobilized, and lacerations can occur in its inner layer, allowing the formation of thrombus.

The HeartFlo™ is a multi-suture instrument for anastomosis with wires automatically applied in end-to-side and side-to-side anastomosis. The surgeon manually ties the suture wires (10 wires) and concludes the anastomosis similarly to the traditional process. Besides of being a product of complex handling, it makes suture in anastomosis (keeping the undesirable foreign body in the internal origin of the anastomosis) and is restricted to end-to-side and side-to-side anastomosis. There is also an excessive mobilization of graft, and can cause lesions in its intimal layer, which would be the inductor that forms the thrombus.

Another technique and known device is the Solem Graft connector, produced by the Swedish company Jomed. It is constituted by a stent made of nickel and titanium coated with polytetrafluorethylen used to connect the internal thoracic artery the left anterior descending coronary artery. The results has not been satisfactory, because it poses risk of bleeding; there is also an excessive mobilization of graft, probably damaging intimal layers, allowing the formation of thrombus; it is not flexible, by this fact, causes trauma to grafts; it does not make multiple anastomosis, at a single time; presents contact with blood flow (foreign body); and is frequent the need of-operations.

The Magnetic Vascular Positioner System is produced by Ventrica and comprises 4 magnetic rings and the anastomosis is processed by magnetic attraction of 4 ports. However, initial experimental results demonstrate leakage, also a undesired contact of materials with blood flow. On the other hand, it is necessary to be careful to avoid the capitation of excess of tissue among the magnets. With this system, there is also a need of suture in some cases; there is occurrence of infarction caused by equipment; and is frequent the need of-operations in patients; and also requires clamping.

Also, as a device known by the medical area, the Combined Anastomotic Device and Tissue Adhesive, developed by Grundeman & Borst group, combines micro mechanical technique with use of adhesive (glue). The use of this method can result in leakages and need traditional sutures; it is frequent the need of reoperation due to leakage/bleeding; and performs only one anastomosis at a time.

Finally, it is also experimentally practiced anastomosis assisted by laser, where the results are not different from conventional isolated sutures, because there is a need of suture in some cases; there is a risk of bleeding e leakage; and does not perform multiple anastomosis.

Even so divulged nowadays, anastomosis with clamper, by insecurity, and almost totality of surgeons perform conventional sutures throughout the route of anastomosis, with an intention of avoiding leakages and bleedings, it means the use of dampers just makes the procedure more expensive, once the conventional suture is also applied.

In short, the conventional anastomosis, with clamping and with suture, standardized in 1906 by Alexis Carrel, remains the first choice for any type of anastomosis and organs to be anastomosed.

With an expectation of changing the current situation, the Brazilian patent no. PI 9706197-2, describes and claims a prosthesis for vascular anastomosis, or in any other organ or tissue, without the use of clamping and sutureless, solving, in an elegant and efficient manner, the limitations inherent to prosthesis of the above mentioned prior art, when used in vascular anastomosis performed, mainly in thin aortas, calcified and friable; or in any other application where a clamping of a vein or artery can pose excessive trauma for conditions of a given patient. The prosthesis that is subject of that request allows the embodiment of fast and safe anastomosis, without obstruction of vein or artery lumen of which anastomosis is made, also allows anastomosis in tissues, veins or arteries in bad conditions and never would accept a clamping used in conventional anastomosis. This is achieved by a generally cylindrical shaped prosthesis with a flange orthogonally extending from its external side wall, in a point in the prosthesis length between its ends; the referred flange has openings distributed around its surface. The description of the usage method and specific construction of the prosthesis is presented in the drawings of the descriptive report of that request, as well as the document C19706197-2, Certificate of Addition of the first.

Although these anastomotic devices can be presented as suited to the purposes for which they were projected, they are not so suited for the purposes of the present invention, as described herein below.

SUMMARY OF THE PRESENT INVENTION

The present invention refers to the variations of the currently known anastomotic devices so as to make possible multiple latero-lateral, termino-terminal and termino-lateral anastomoses without clamping and sutureless or with a quick clamping and sutureless if the organ presents normal walls, where a vascular graft or any other is inserted into the lumen of each prosthesis and turned by casing in order to cover part of it, which will remain inside the graft (vein, artery or tissue), being fixed onto the tubular member of the prosthesis by a circular stitch. The flange of the prosthesis has a number of spaced-out openings in its periphery, allowing the prosthesis to be sutured only for its fixing onto the tissue, vein, artery or any other organ outside the anastomosis. Besides, the flange of the prosthesis also has at least one lateral insert that allows the prostheses to be tightly united one to the other. The prosthesis may also have varied dimensions and shapes to simultaneously accommodate grafts of varied sizes and types.

One objective of the present invention is to produce an anastomotic device of multiple lateral inserts having a tubular member and a flange allowing the configuration of the most varied types of anastomotic sets of different types and calibers (for instance, prosthesis with anastomotic trunk—formed by the union of several grafts by one of its extremities—in the wanted extension and diameter, sufficient to cover the intraluminal part of the prosthesis. The anastomotic trunk may be made with autologous, homologous, heterologous or synthetic biological grafts.

Another objective of the present invention is to produce a board of prostheses including a flange with multiple intraluminal parts or with multiple holes through which intraluminal or occluding parts will be inserted, according to the need of the anastomosis to be carried out.

Additional objectives of the present invention and other modalities will come up as the description continues. These modalities will be described in sufficient detail to allow experts in the matter to implement the invention. Moreover, it must be understood that other modalities may be used and that structural changes may be carried out without distancing themselves from the scope of the invention. In the accompanying drawings, reference characters of similar reference designate the same or similar parts through all the several views. The following detailed description, thus, is not to be taken in a limiting sense and the scope of the present invention is better defined by the annexed claims.

BRIEF DESCRIPTION OF THE DRAWINGS

For the invention to more fully understood, it will be now described through examples regarding the annexed drawings, of which:

FIG. 11A illustrates the prosthesis board with the double intraluminal part and the round flange with double outlet.

FIG. 11B illustrates the upper view of the prosthesis board of FIG. 11A with double intraluminal part, showing the holes through which the stitches will pass to facilitate fixing the grafts to the intraluminal parts.

FIG. 12A illustrates the prosthesis board with double intraluminal part and non-round flange, with the possibility of being either elliptical or rectangular.

FIG. 12B illustrates the upper view of the prosthesis board of FIG. 12A, with double intraluminal part, showing the holes through which the stitches will pass to facilitate the fixing of the grafts to the intraluminal parts.

FIG. 13A illustrates the prosthesis board with triple intraluminal part and round flange with triple outlet.

FIG. 13B illustrates the upper view of the prosthesis board of FIG. 13A, with triple intraluminal part, showing the holes through which stitches will pass to facilitate fixing of the grafts to the intraluminal parts.

FIG. 14A illustrates the prosthesis board with threaded, double, removable intraluminal part and round flange with double exit.

FIG. 14B illustrates the upper view of the prosthesis board of FIG. 14A, with threaded, double intraluminal part, showing the holes through which will pass the stitches to facilitate fixing of the grafts to the intraluminal parts.

FIG. 15A illustrates the prosthesis board with threaded, double, removable intraluminal part and non-round flange, with the possibility of being either elliptical or rectangular.

FIG. 15B illustrates the upper view of the prosthesis board of FIG. 15A, with threaded, double intraluminal part showing the holes through which will pass the stitches to facilitate fixing of the grafts to the intraluminal parts.

FIG. 16A illustrates the prosthesis board with triple, threaded and removable intraluminal part and round flange with triple outlet.

FIG. 16B illustrates the upper view of the prosthesis board of FIG. 16A, with intraluminal, triple, threaded part showing the holes through which will pass the stitches to facilitate fixing of the grafts to the intraluminal parts.

FIG. 17A illustrates the prosthesis board with double, fixed, beveled intraluminar part and round flange with double outlet.

FIG. 17B illustrates the prosthesis board with threaded, double, removable and beveled intraluminal part and round flange with double outlet.

FIG. 18A illustrates the prosthesis board with double, fixed, beveled intraluminal part, with the possibility of being either elliptical or rectangular.

FIG. 18B illustrates the prosthesis board with double, threaded, removable, beveled intraluminal part, and non-round flange, with the possibility of being either elliptical or rectangular.

FIG. 18C illustrates the upper view of the prosthesis board of FIG. 18A, with double, fixed or removable, beveled intraluminal part, showing the holes through which will pass the stitches to facilitate fixing of the grafts to the intraluminal parts.

FIG. 19A illustrates the prosthesis board with triple, fixed, beveled intraluminal part and round flange with triple outlet.

FIG. 19B illustrates the prosthesis board with triple, threaded, removable and beveled intraluminal part and round flange with triple outlet.

FIG. 19C illustrates the upper view of the prosthesis board of FIG. 19A, with triple, fixed or removable, beveled intraluminal part, showing the holes through which will pass the stitches to facilitate fixing of the grafts to the intraluminal parts.

FIG. 20A illustrates the prosthesis board with triple intraluminal part (with the possibility of being double or having any other number), either fixed or removable, beveled, with round flange with double outlet and a tubular body before the intraluminal part, so as to cause grafts to contact each other before leaving the prosthesis.

FIG. 20B illustrates the upper view of the prosthesis board of FIG. 20A.

FIG. 21A illustrates the prosthesis board with triple intercommunicable intraluminal part in the shape of a clover, beveled and round flange with double holes on the surface of the flange to fix the graft and the organ.

FIG. 21B illustrates the upper view of the prosthesis board of FIG. 21A.

DESCRIPTION OF THE FAVORITE MODALITIES

Figure 1:
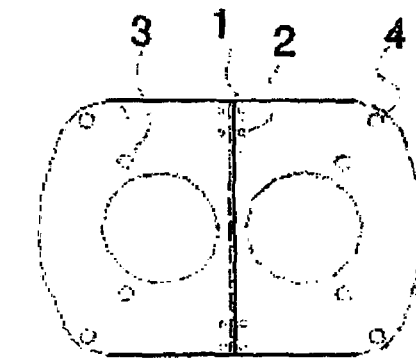
FIG. 1 illustrates one first realization of the prosthesis for anastomosis equipped with flanges with lateral inserts so as to form the most different types of prosthetic sets.
Figure 1:
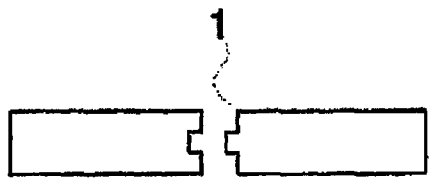
Figure 1:
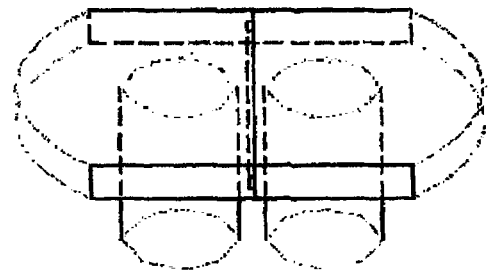

In regards with the drawings, in which similar reference characters indicate similar elements for all views, the figures illustrate one of the realization forms of the present invention in the form of prosthesis for anastomosis with flanges having multiple inserts to form a set of prostheses and of a prosthesis board to make flexible the use of the wanted intraluminal parts.

FIG. 1 presents a prosthesis made up of two parts united by lateral, tightly closed insert 1 and stitches in its flanges. Each part has half a flange and a tubular member orthogonal to it. The flange formed by the junction of the two parts has internal 3 and external 4 holes, tabs or double holes or fold (the latter ones are not shown) and also small, juxtaposed holes 2 situated on the periphery of each half of the flange, through which threads (made of steel, silk, polypropylene, etc.) will pass to reinforce the union of the parts. The tubular member has at least one groove on its external surface, where the grafts will be anchored after eversion (already shown). The double holes, tabs or fold of the flange have the purpose of anchoring the tabs of the threads on their way through the internal holes on the upper surface of the flange.

Figure 2:
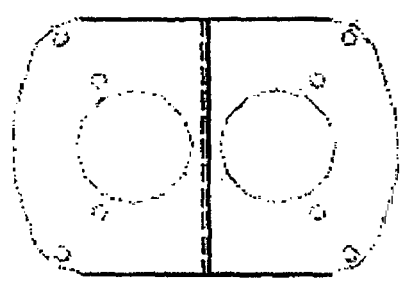
FIG. 2 illustrates a second realization of the prosthesis for anastomosis equipped with flanges with lateral inserts so as to form the most different types of prosthetic sets, in which the intraluminal parts may be either fixed or removable and threaded.
Figure 2:
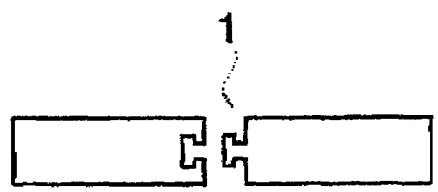
Figure 2:
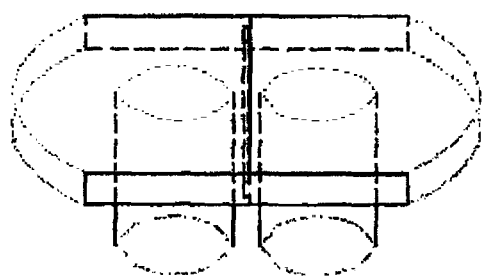

FIG. 2 represents another type of lateral, tightly closed insert 1 between the flanges, giving stability and dispensing with the use of stitches passed through the juxtaposed holes of the periphery of each part of the flange. Again, the double holes or external tabs or fold (small extension of the tubular member over the flange) are not shown on the flange. It shows that there is no need of small juxtaposed holes of the flange.

Figure 3:
FIG. 3 illustrates one third realization of the prosthesis for anastomosis equipped with flanges with inserts in the diametrical direction, so as to form circular prosthetic sets, in which the intraluminal parts may be either fixed or removable and threaded.
Figure 4:
FIG. 4 illustrates one fourth realization of the prosthesis for anastomosis equipped with flanges with inserts in the diametrical direction, having small holes for better fixing of the parts so as to form circular prosthetic sets, in which intraluminal parts may be either fixed or removable and threaded.

FIG. 3 and FIG. 4 present only different forms of their flanges or their halves (respectively circular and semicircular), whereas in FIG. 3 the same insert is kept as in FIG. 1 with the small juxtaposed holes 2 and, in FIG. 4, only the same type of insert of FIG. 2.

Figure 5:
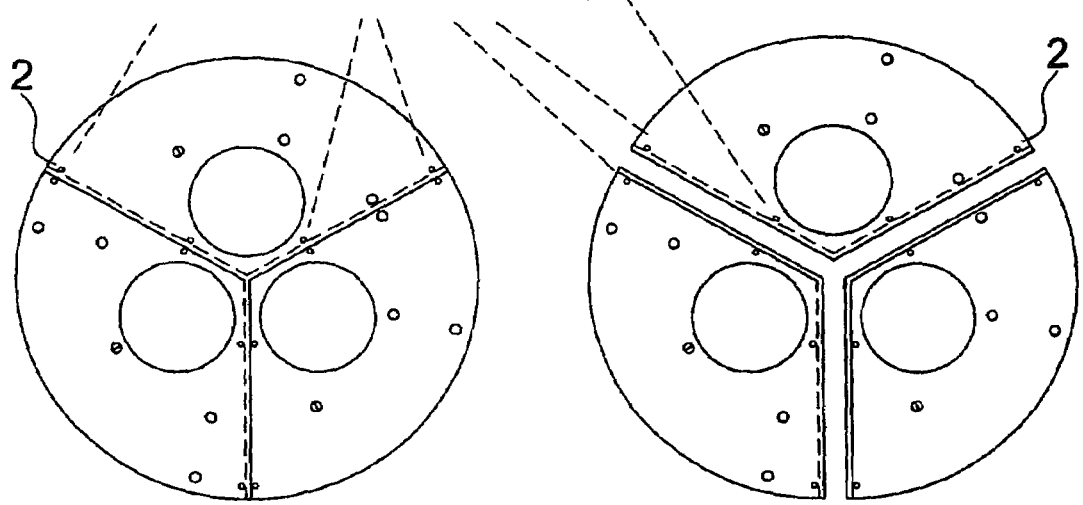
FIG. 5 illustrates the fifth realization of the prosthesis for anastomosis equipped with flanges with inserts in the axial direction so as to form circular prosthetic sets, in which intraluminal parts may be either fixed or removable and threaded.
Figure 5:
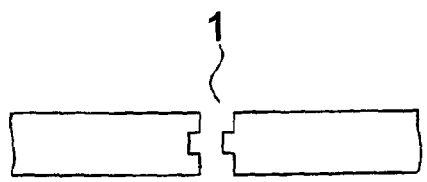

FIG. 5 shows a prosthesis with circular flange split into 3 parts, each having a segment of the flange with multiple holes and a tubular member. These segments of the flange are tightly inserted, forming a single flange, being fixed through stitches (stainless steel, polypropylene, silk, etc.) passed through small juxtaposed holes located next to their insert edges. In this flange have been shown internal holes, the external holes (for double suture of the prosthesis to the organ wall), the interposed holes between the internal holes (to anchor the thread tabs into the flange surface, avoiding that they block the lumen of the prosthesis tubular members) and the small juxtaposed holes 2, whose stitches make sure that the three parts of the prosthesis will be united. In this prosthesis, two parts might be inserted with the insert represented in FIG. 4 and only the last one to be simultaneously inserted into the other two, such as the insert of FIG. 3 or 5, needing the small juxtaposed holes.

The prostheses of FIGS. 1-5 have their tubular members covered by graft that passed through their lumen, was everted and fixed to it with an external circumferential stitch or by any other method. The technique on the use of these techniques consists in passing at least two opposed stitches in U with parallel legs, from up down through the internal holes, anchored in the middle by double holes, tabs or fold; to transfix or not the wall of the organ in the place of the anastomosis (whose incision size, if rectilinear, will be equal to half the total perimeter of tubular members of the prosthesis) and return or not to the external hole of the flange, from down up, if it is wanted to make a suture of the flange at the friable walls, reducing its mobilization. Thus, the threads will be tied, compressing the organ wall over the tubular members or over the upper surface of the single flange. Also, these threads fix the parts of the prosthesis among themselves and provide greater stability.

Figure 6:
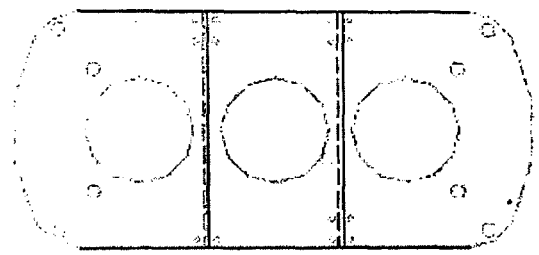
FIG. 6 illustrates the sixth realization of the prosthesis for anastomosis equipped with flanges with inserts in the longitudinal direction so as to form insertable prosthetic sets on a right line, in which the intraluminal parts may be either fixed or removable and threaded.
Figure 6:
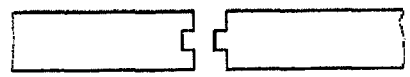
Figure 6:
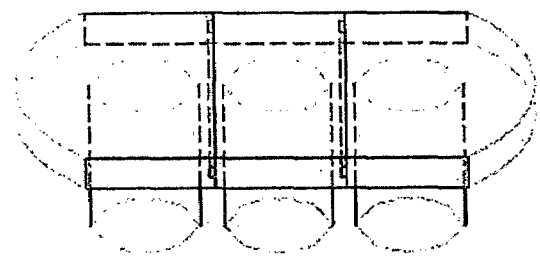
Figure 7:
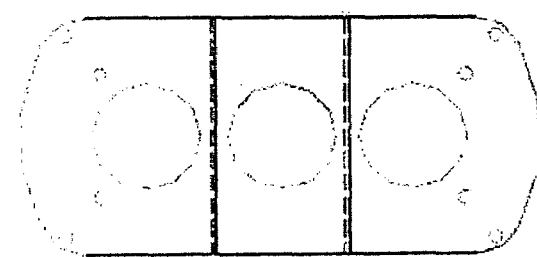
FIG. 7 illustrates the seventh realization of the prosthesis for anastomosis equipped with flanges with inserts in the longitudinal direction so as to form insertable prosthetic sets on a right line, in which the intraluminal parts may be either fixed or removable and threaded.
Figure 7:
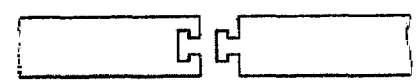
Figure 7:
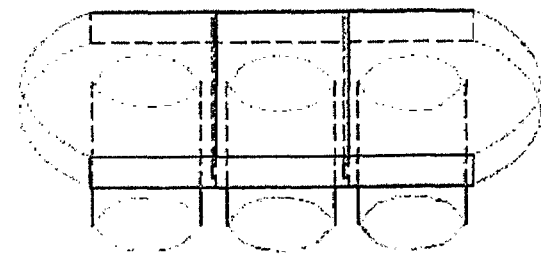

FIGS. 6 and 7 show a prosthesis with three parts aligned and inserted in the same ways as described. Its use technique is also similar to that described above. This configuration is especially indicated for small-diameter organs and can be made in multiple anastomoses in series and aligned at one time, without clamping and sutureless. These prostheses have transversal external grooves on their tubular members to avoid that the everted grafts circumferentially fixed to them flow off. All their edges are blunt, not cutting ones.

Figure 8:
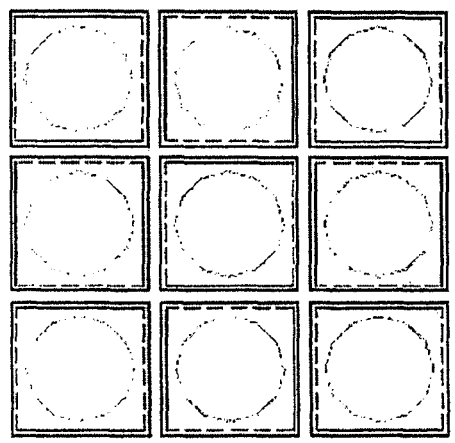
FIG. 8 illustrates the eighth realization of the prosthesis for an anastomosis equipped with flanges with inserts in every direction so as to form sets of insertable prostheses in any position and number, where intraluminal parts may be either fixed or removable and threaded, being beveled in one, two, three or four bevels.
Figure 8:
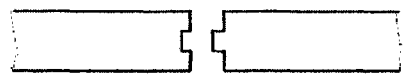
Figure 8:
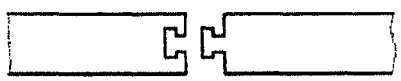
Figure 8:
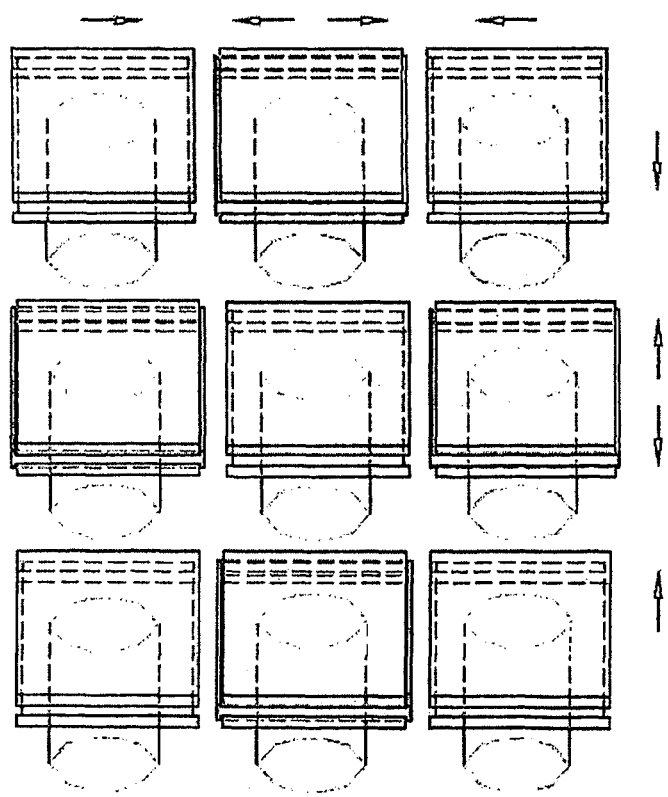

FIG. 8 represents a series of independent prostheses with tightly shut lateral inserts on their flanges, and may be inserted by all their edges to similar ones or which are multiple in the extension of their flanges. Any configuration is possible: aligned, triangular, trapezoidal, square, rectangular, etc., and the shape of their flanges may very, such as: semicircular, fitting into another bigger, circular one by touching it; circular with touching circulars, etc. Any shape of slotting and final shape of its flanges is possible, such as the composition of a puzzle fitting together. It must be said that any one of them is independent and may be used in isolation. Here its tubular members are orthogonal and set to the flange. Neither the flange holes nor the double holes, small juxtaposed holes or the transversal grooves of the tubular members have been shown. The technique for is use, once the prostheses-grafts sets have been assembled, is similar to the described above. It is important to stress that the final composition to be given may be chosen at the time of the anastomotic procedure, depending on the shape, diameter and conditions of the organ that will receive it.

Figure 9:
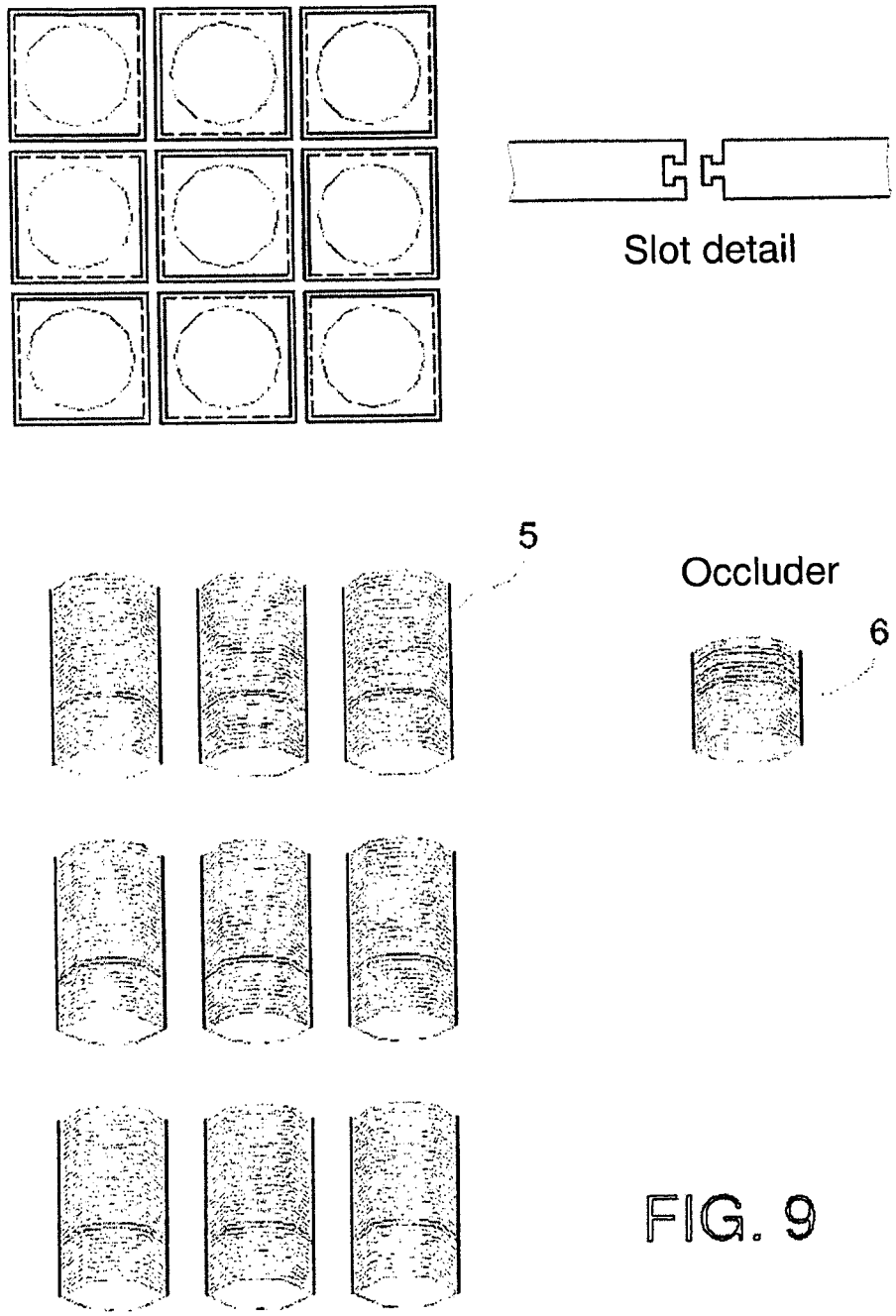
FIG. 9 illustrates the ninth realization of the prosthesis for anastomosis equipped with flanges with inserts in every direction so as to form sets of insertable prostheses in any position and number in which the intraluminal parts may be either fixed or removable and threaded, while also having occluders to plug the holes that are not used.

FIG. 9 represents a set of independent prostheses with tightly shut lateral inserts on is flanges, but differs from that of FIG. 8 in that its tubular members are separated from the flange and threaded externally to the lumen of the flange that has an internal thread 5. It also shows an occluder device 6 without lumen, with external threading, that may plug any hole of the flange one does not wish to use anymore. The prosthesis-graft set may be assembled after the total threading of the tubular member into the flange and, thus, the graft will be everted and circumferentially fixed to its external surface. Or the graft may initially pass by the flange lumen and be fixed to it with stitches from the graft to its holes. Next, the graft is retrogradely passed by the lumen of the tubular member, which will then be smoothly threaded to the flange while the graft is everted on it. This would allow, even after the anastomosis is made, a tubular member to be removed and replaced by an occluder. The use technique is the same as the one described above.

Figure 10:
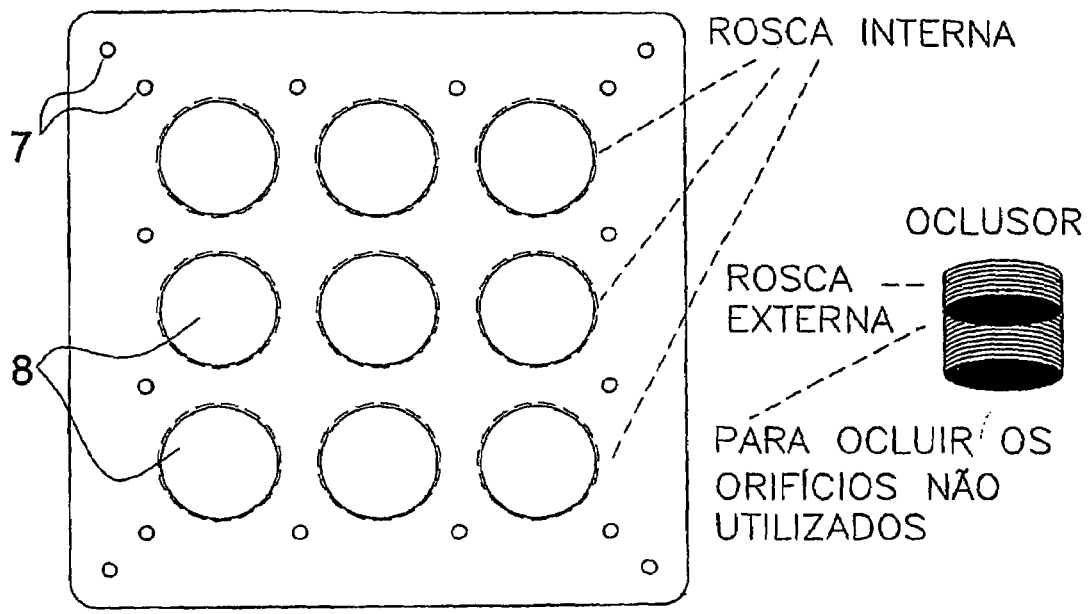
FIG. 10 illustrates a board of prostheses with threaded holes and the intraluminal parts may be either fixed or removable and threaded, also having occluders to plug the holes that were not used.
Figure 10:
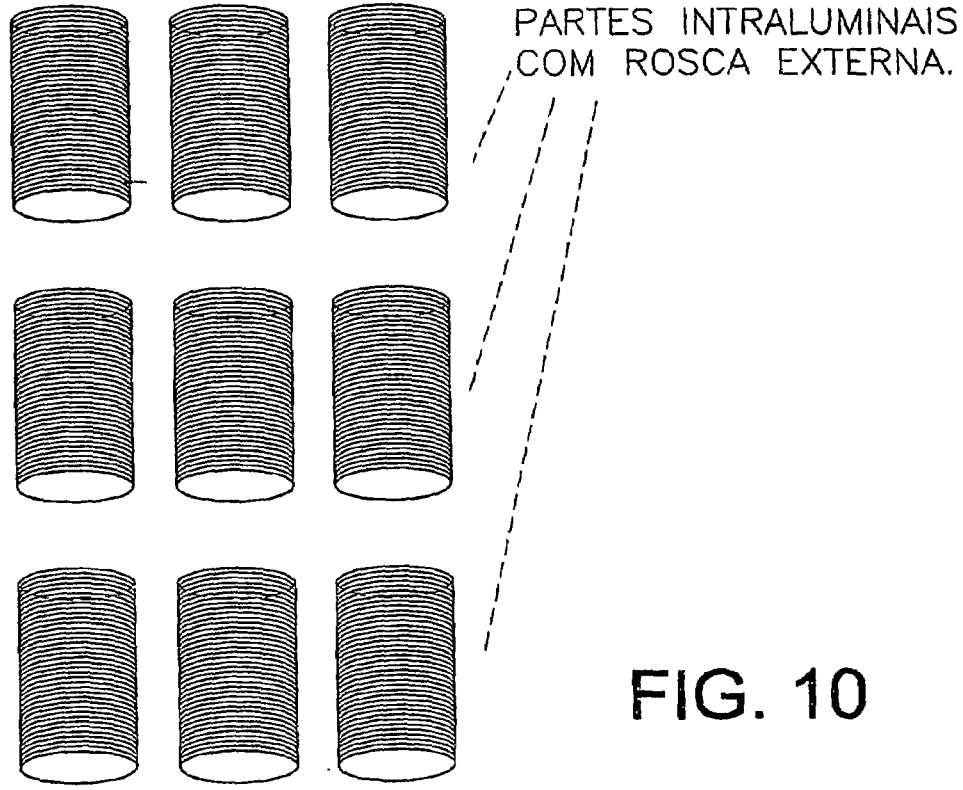

FIG. 10 represents the so-called prosthesis board for anastomosis including a big flange, either square or of another shape, with multiple holes 7 in is periphery and multiple threaded center lumens 8, which might be dispersed by means of any drawing or randomly, through which also externally threaded tubular members will pass. It is possible to use the wanted number of lumens, occluding the others with occluders (tubular members without lumen and externally threaded). In this board, the lumens 8 may have variable calibers and may separately receive grafts of any caliber. The technique for its use is the already described one, both in the form to fix the grafts to the flange or to the tubular members.

FIGS. 11A to 13B represent prostheses with two and three tubular members 9 fixed to the flange, which, besides the holes mentioned above, have small holes 10 on the touching spot between the tubular members through which fine threads will pass from up down and unite the edges of the grafts drawing them to the lower surface of the flange, making easier their eversions and, next, binding them around the tubular member in order to circumferentially fix them onto their external grooves. The technique for their uses is the same.

FIGS. 14A to 16B represent prostheses that differ from the prostheses of FIGS. 11A to 13B as their tubular members are separated from the flanges and they are threaded up to the wanted depth. Here the grafts may initially be united by their extremities to the center of the lower face of the flange by stitches passed through the small holes 10 existing there. Tubular members 9 are then threaded up to the wanted height while being coated by the everted grafts. At the end of the threading, the thread lines bind the grafts on the tubular members and fix them circumferentially.

Figure 17C:
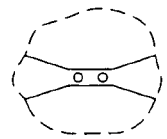
FIG. 17C illustrates the upper view of the prosthesis board of FIG. 17A, with double, fixed or removable, beveled intraluminal part, showing the holes through which the stitches will pass to facilitate fixing of the grafts to the intraluminal parts.

FIGS. 17A to 17C represent prostheses that differ from the prostheses from FIGS. 14A and 14B as their tubular members have a bevel 11 inwards, although they could be doubly, triply and quadruply beveled. These bevels are important as they increase the origin area of the anastomosis while facilitating their future characterizations should it be necessary, for instance, in hemodynamic restudies, especially if they are made with radiographically opaque material. They may be tubular members fixed to the flange as in FIG. 17A of threaded as in FIG. 17B.

The prostheses from FIGS. 18A to 18C differ from the prostheses of FIGS. 17A and 17C only in that they have oval or rectangular flanges with round corners.

The prosthesis of FIG. 19A differs from the prostheses of FIG. 13A in that they have their tubular members beveled to increase the origin area of the anastomosis and facilitate its catheterizations at least by the fact that the lower edge of the bevel is in the intima of the organ wall to which it was fixed.

The prosthesis of FIG. 19A differs from the prosthesis of FIG. 16A in that its tubular members are beveled for the reasons already mentioned.

FIG. 19C is an upper view of FIGS. 19A and 19B.

Up to here, the prostheses shown have their grafts individualized on their course through the interior of the tubular members. Now, the prostheses of FIGS. 20A and 20B have a segment 12 common to the tubular members, having the same small holes on the spot and height where the tubular members lose their individuality. This triple tubular member in a single piece may have its intraluminal parts either beveled or not. This triple tubular member in a single piece may be either fixed or have threads in its common part and be threaded to the flange at one time. This common segment of the tubular members, whose diameter is equal to the sum of the diameters of the tubular members in isolation, cause the grafts to relate among themselves before emerging from the prosthesis. The fact that they individualize themselves inside the lumen of the prosthesis increases the versatility of the direction of these grafts upon leaving the prosthesis, allowing them to be directed to any position with zero risk of shoving. The grafts may be united in a touching point to the three, to be retrogradely introduced in the lumen of the tubular members with the threads passing by the small central holes, to be fixed to the lower surface of the prosthesis, to be everted and again circumferentially fixed by those same threads. This allows for a considerable time saving, making unnecessary the confection by suture or another method of the anastomotic trunks, while also avoiding the inadvertent exposition of the threads in the lumen of the grafts, besides reducing the risk of bleeding, as there are no suture lines between them. The prosthesis of FIGS. 20A and 20B makes very simple and quick the confection of a termino-lateral, ample, multiple anastomosis at one time with a single prosthesis, without clamping and sutureless. Its use technique is similar to the previous ones, as well the holes of its flange.

The prosthesis represented by FIGS. 21A and 21B has some very singular characteristics. It has a flange with only four double equidistant holes 13. It has a triple tubular member, beveled inwards, but a single lumen. To coat the tubular member, it is necessary the confection of an anastomotic trunk that will also be everted and externally fixed to the tubular member through stitches passed by its holes situated in the thickness of the tubular member or by the small tabs external to it, adjacent to the flange or even small holes or tabs situated on the flange. If they are tabs, they are fixed to its lower surface. In order to be well adjusted to the tubular member, the tabs or holes must also be present in the groove formed by the junction of the two tubular members. This clover-like drawing keeps the original form and diameter of the grafts as if they were individualized, which is important from the physiological point of view, differently from forming a single mouth, which might take up a triangular form, not a circular one. A great advent is represented by just these four double holes 13. The threads would be previously tied to the double holes 13 in their lower surface, their legs would be fixed and there would not be more thread tabs situated on the upper surface of the flange, making unnecessary double holes, tabs or folds to anchor them, besides bringing to an end the concern over interposition of the prosthesis lumen by thread tabs. This previous fixing of the threads to the flange would render the procedure quicker and safer, making the risk that the threads break up at the moment they are tied almost null, as their tabs would not undergo friction against the edges of the hole. Here, differently from what has been described, a thread tab must never be tied with another of the same thread, but with one of the adjacent thread. Thus, threads with different colors will make applying the technique even easier. Contiguous tabs of different colors must always be tied among themselves. Thus, in this case, each thread will have its two tabs passed together, almost at the same point. Next, an incision is made in the middle of the parallel and opposed legs of the threads and this without risk that they are cut out even if the organ wall is longitudinally and/or transversally cut, crisscrossing the center of the anastomosis. Finally, the anastomotic set is introduced and the legs of the different threads are tied up two by two, compressing the organ wall over the triple tubular member, making sure that a perfect hemostasia is produced, if it is a vessel. Also here, the anastomosis may be without clamping and sutureless, termino-lateral or terminoterminal.

Figure 22A:
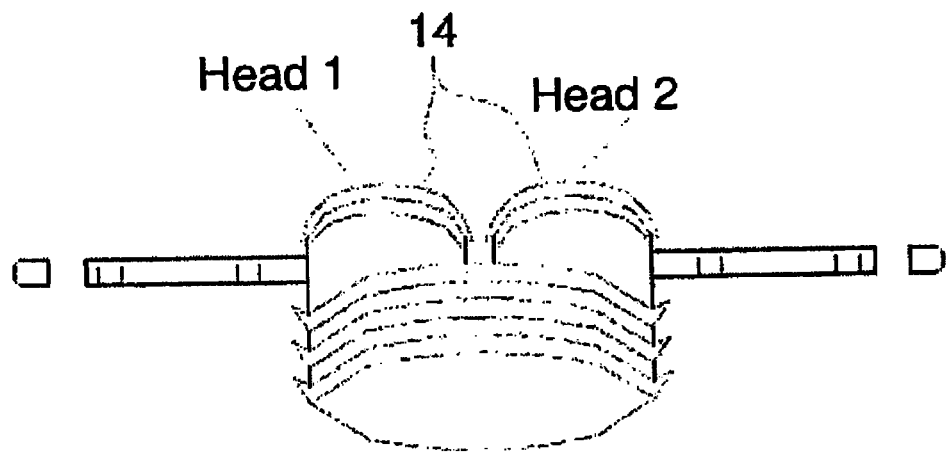
FIG. 22A illustrates a prosthesis board with two heads (medusa head) by intraluminal part, where grafts are individually connected.
Figure 22B:
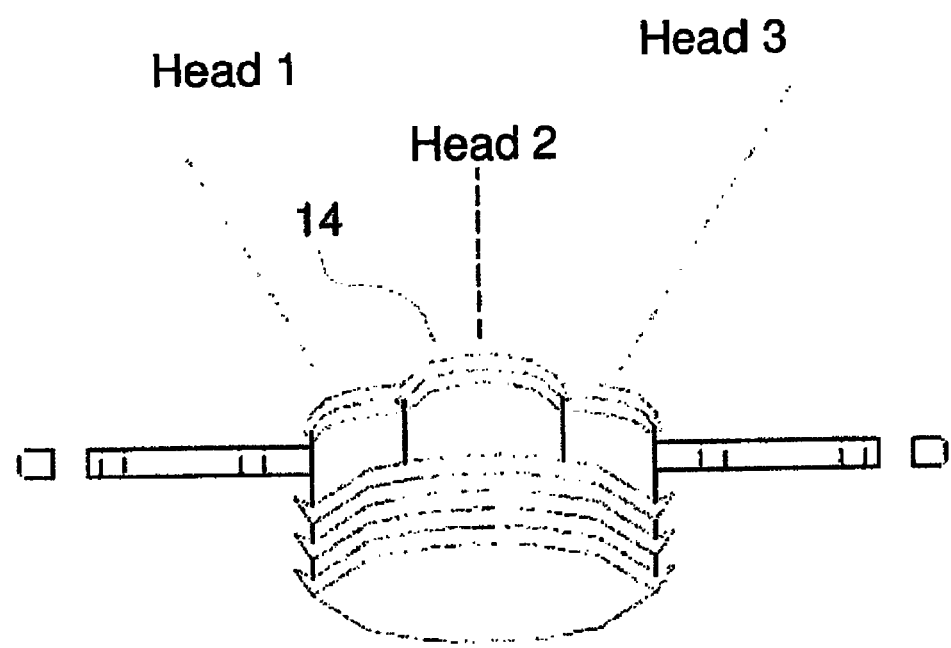
FIG. 22B illustrates a prosthesis board with three heads (medusa head) by intraluminal part, where grafts are individually connected.

The prostheses of FIGS. 22A and 22B are of a thick caliber in their origin and low profile or thickness (a few millimeters). They may have their heads 14 either aligned or in the form shown. The heads are movable with a rigid extremity. Thus, their intraluminal part may have an oval or elliptical form, always having transversal grooves, as shown. This way, they may be used without coating of their intraluminal part, with their heads being externally covered by the grafts (fixed to their rigid part), which may be of any type, preferably autologous. Due to the fact that they have a low profile, thick caliber and probable high laminar flow, thanks to the perfect cylindrical form provided by the prosthesis, the risk of their being obstructed by thrombogenicity related to the contact with the foreign body (prosthesis material) with the blood, in the case of vascular anastomoses, is considerably reduced.

Obviously, it may be used as already described, with its intraluminal part covered by everted anastomotic autologous trunk fixed to it circumferentially. In this case, the grafts would pass retrogrately by the lumen of the tubular member and heads 14. Also its use technique is similar to that of the prostheses that do not have threads for their fixing previously tied to their flange.

Figure 23A:
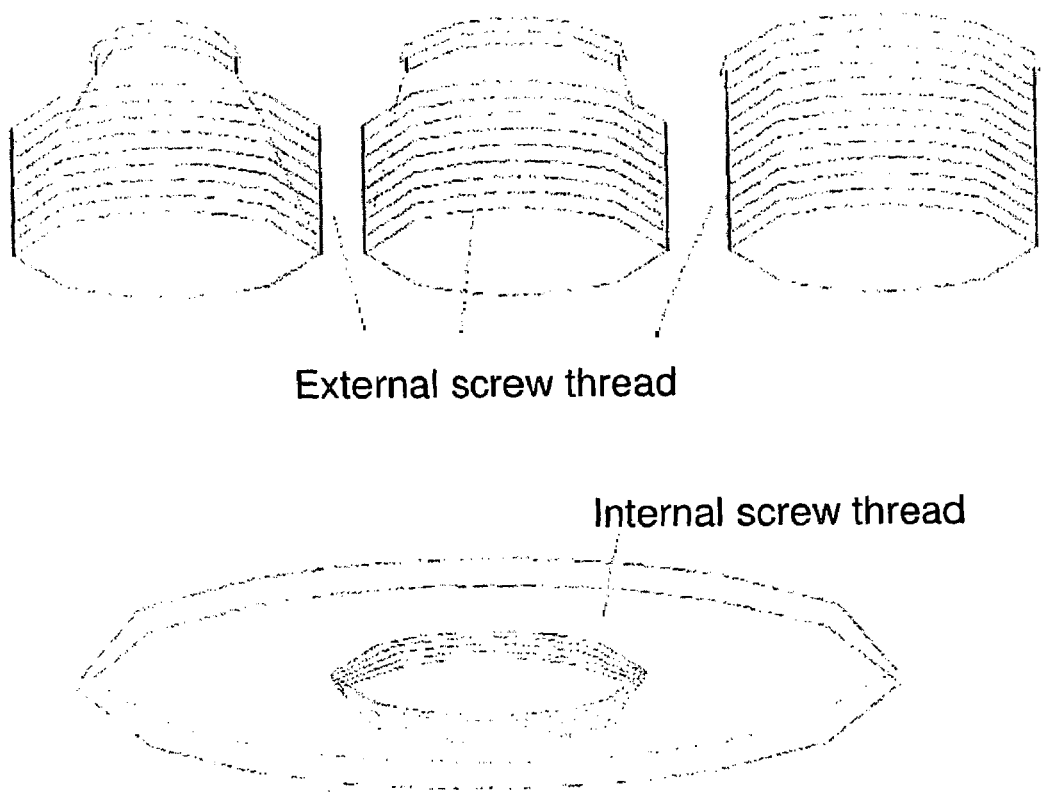
FIG. 23A illustrates a single head for a simple prosthesis and a prosthesis board, the single head being of a variable caliber for one same caliber of calibrous and short and removable intraluminal part threaded to the flange without intraluminal part.

FIG. 23A represents a prosthesis with flange and tubular member separated and united by threading between them. The flange has lumen with internal screw thread and, externally, the tubular member. Tubular members, when completely threaded, are at one internal extremity and at an external one. The internal, intraluminal extremity will always have the largest possible diameter so as to allow the lumen to pass from the flange. The external extremity may have its diameter equal to or smaller than the internal one, never larger than it. When the external diameter is smaller, the interior of the tubular member has the shape of a cone trunk so that the flow can be laminar in vascular anastomoses. Several tubular members may pass by the same flange with an external extremity of very small diameter or even a maximum diameter equal to that of its internal extremity. The reason for this is to always allow the confection of proximal anastomoses with ample origin even if the grafts are fine. Conventional anastomoses with fine grafts, besides being technically difficult, are shortly lived, often closing immediately after their conclusion. Here, it becomes very simple to anastomize without clamping and sutureless, termino-lateral, even a graft with a diameter shorter than 1 mm. If the used tubular member has internal and external extremities with the same diameter, that is, the maximum one, it is preferred that the graft or anastomotic trunk passes by the lumen of the prosthesis, in case it is everted, that it covers the intraluminal part and that it be circumferentially fixed to it. This way, if the grafts are autologous, there will be no foreign body in the origin of the anastomosis, which is the ideal condition, besides the fact that the anastomosis is multiple, at one time, ample, without clamping and sutureless. When grafts coat the heads externally, once the anastomotic set is introduced in the lumen of the organ, the tubular member may be partially unthreaded in order to guarantee its complete absence of protuberance in the lumen of the organ. This flange may have, preferably, only double holes, or have internal, external, double holes, tabs or folds. Thus its use technique will depend on how its flange is shown. These techniques have already been described. Obviously, any type of graft may be used with this prosthesis or any of those mentioned above.

Figure 23B:
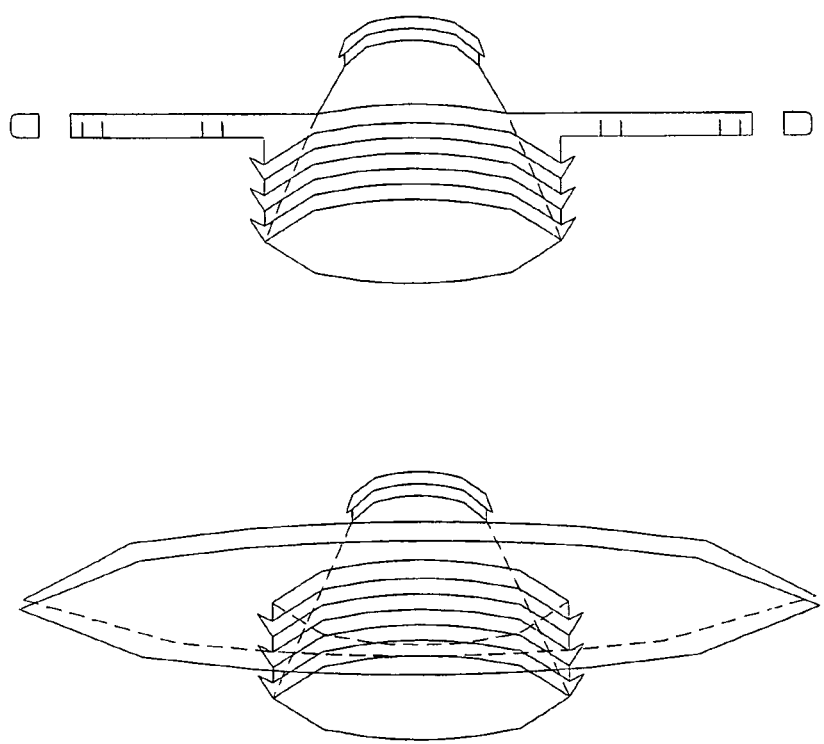
FIG. 23B illustrates a single head for a simple prosthesis and for a prosthesis board, the single head being of a variable caliber for the same caliber of calibrous and short, removable and threaded intraluminal part to the flange with intraluminal part.

FIG. 23B represents a prosthesis with flange and an asymmetric tubular member fixed orthogonally to it, with a calibrous internal part and an external one of a smaller caliber. It differs from the prosthesis of FIG. 23A in that it does not have its versatility to allow the use of several tubular members with calibers equal to or different than its internal and external parts. Also here, the interior of the tubular member has the form of a cone trunk, which, in the case of vessels, guarantees the use of a laminar, not whirling flow, which would occur if there were an abrupt reduction at right angles of the caliber of the internal, larger part, to the caliber of the smaller, external part. This prosthesis must have a low profile (few millimeters in total thickness, including the external part, the flange and the internal part) and be as calibrous as possible in its origin. Thus, even small-caliber grafts may cover the external part being fixed to them and be safely used while making terminolateral anastomoses without clamping and sutureless. This calibrous origin, besides guaranteeing longer life to the graft, also facilitates catheterization of the prosthesis lumen in contrasted studies like cardiac catheterization. Made in radiographically opaque material, not even in microanastomoses, it will be difficult to locate the origin of the anastomosis and selectively catheterize it, which would significantly reduce costs, due to the smaller amount of radiographic opaque contrast and, especially, due to the risk of toxic complications (kidneys, etc.) presented by those contrasts. The technique of its use will also depend on the presentation of its flange, again, if only with double holes or with multi internal-external holes, double holes, tabs or folds. Thus, in this prosthesis, the fluid will get in touch with the material with which it was made, which should be as biocompatible and inert as possible.

Figure 24:
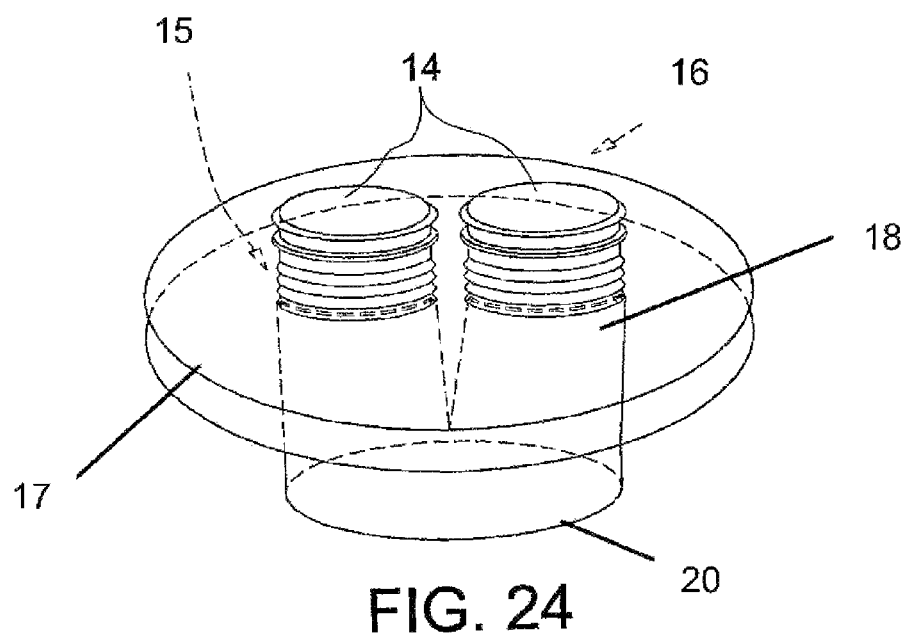
FIG. 24 illustrates a double head for a simple prosthesis and for a prosthesis board, the double head having a pleated, flexible, movable extremity.
Figure 25:
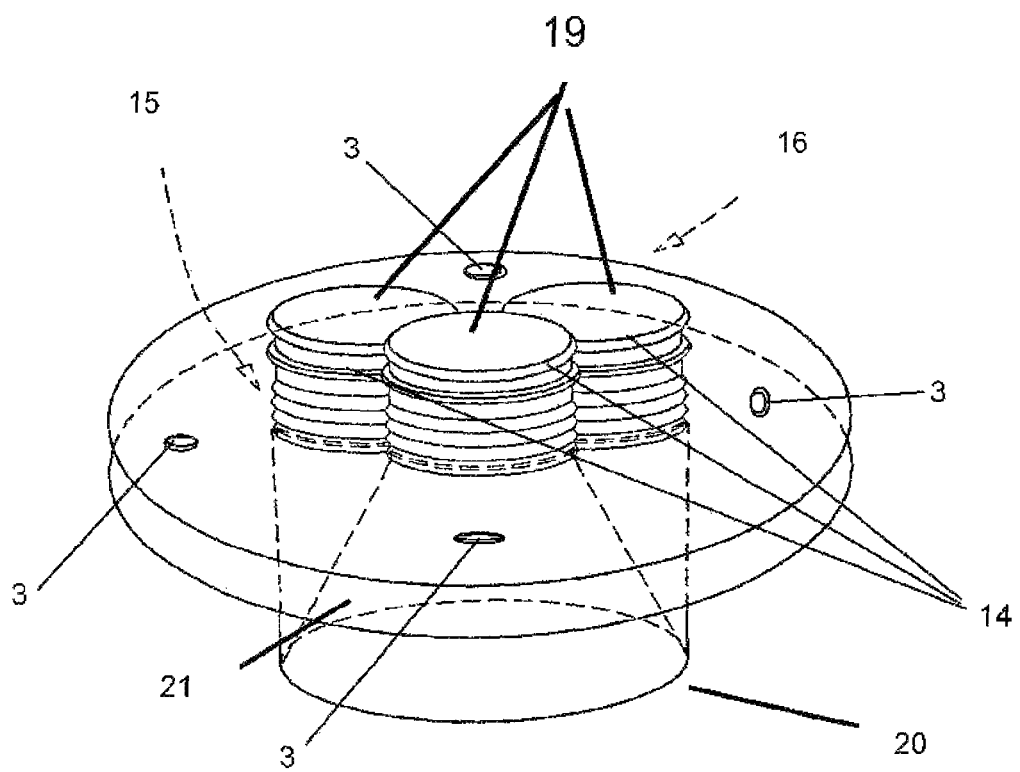
FIG. 25 illustrates a triple head for a simple prosthesis and a prosthesis board, the triple head having a pleated extremity of discreetly smaller calibers than those of the grafts that will cover them, and the prosthesis lumen having the shape of a cone trunk in its interior.

The prostheses shown by FIGS. 24 and 25 are in a single piece, with single flange 17 extending from a lateral wall 18 of an intraluminal tubular member 20 and extraluminal double or triple heads 14 of the lumen 16 having through openings 19. The tubular member 20 also has a conic internal form 21 directed to each head. The heads 14 may be either pleated, flexible or with rigid extremity. They may be either fixed to the flange by any method, such as suture, glue, by coating the upper circular extremities to the flange and being fixed to them circumferentially, etc. Again, those are prostheses that guarantee a large caliber of the origin of the independent anastomosis of the graft caliber. Also here the fluid will contact the material of the prosthesis. Thus the need that they are of a thick caliber and low profile, minimizing the risks related to this contact: foreign-body type reaction, thrombogenicity, etc. In order to lessen even more such undesirable reactions, those prostheses could be made previously by the industry, with their internal and external surfaces coated, for instance, with homologous, treated and freeze-dried biological tissue. Perhaps, if such prostheses were immersed in those preparations of endothelial freeze-dried cells and had microporous internal and external surfaces, by adding any kind of little antigenic biological glue, their surfaces could remain totally and uniformly coated by such cells, thus lessening said reactions. Also their intraluminal parts might be beveled in one, two, three or four bevels, increasing the anastomosic area even more, rendering the contrasted restudy easier and, fundamentally, reducing the amount of the material that made the prosthesis. The technique for its application is like those already described, according to the flange configuration.

The invention claimed is:

1. A single piece prosthesis for anastomosis, wherein said prosthesis has a low profile, does not use clamping, and is sutureless, the prosthesis comprising:

a single tubular member having a plurality of extraluminal heads and a conical internal form directed to each one of the plurality of heads, the plurality of extraluminal heads are pleated, flexible, and have a rigid extremity; and a single flange extending from a lateral wall of the tubular member, the flange comprising a plurality of perpendicular holes for transfixing the flange, wherein the plurality of perpendicular holes are diametrically opposed and equidistant from each other.

2. Prosthesis, according to claim 1, further comprising an occluder (6) to obstruct non-used intraluminal parts.

3. The prosthesis for anastomosis according to claim 1, further comprising an anastomotic trunk, which may be made with autologous, homologous, heterologous or synthetic biological grafts.

4. A prosthesis for anastomosis, wherein said prosthesis does not use clamping and is sutureless, the prosthesis comprising:

a tubular member having a conical internal form and including a plurality of extraluminal heads, the plurality of extraluminal heads are pleated, flexible, and have a rigid extremity, and a flange extending from the tubular member, the flange comprising: a plurality of perpendicular holes for transfixing the flange, wherein the plurality of perpendicular holes are diametrically opposed and equidistant from each other.

5. The prosthesis for anastomosis according to claim 4, further comprising an anastomotic trunk, which may be made with autologous, homologous, heterologous or synthetic biological grafts.

* * * * *